US006572533B1

(12) United States Patent
Shapland et al.

(10) Patent No.: US 6,572,533 B1
(45) Date of Patent: Jun. 3, 2003

(54) CARDIAC DISEASE TREATMENT AND DEVICE

(75) Inventors: J. Edward Shapland, Vadnais Heights, MN (US); Clif Alferness, Redmond, WA (US); Donald Palme, Princeton, MN (US); Michael Girard, Lino Lakes, MN (US); Donald Rohrbaugh, Minnetonka, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 327 days.

(21) Appl. No.: 09/641,141

(22) Filed: Aug. 17, 2000

(51) Int. Cl.$^7$ .............................. A61F 13/00; A61F 2/00
(52) U.S. Cl. ...................................................... 600/37
(58) Field of Search .............................. 600/16–18, 37, 600/201; 601/11; 623/3, 66; 128/897, 898; 606/151

(56) References Cited

U.S. PATENT DOCUMENTS

| | | | |
|---|---|---|---|
| 3,983,863 | A | 10/1976 | Janke et al. |
| 4,048,990 | A | 9/1977 | Goetz |
| 4,403,604 | A | 9/1983 | Wilkinson et al. |
| 4,428,375 | A | 1/1984 | Ellman |
| 4,630,597 | A | 12/1986 | Kantrowitz et al. |
| 4,690,134 | A | 9/1987 | Snyders |

(List continued on next page.)

FOREIGN PATENT DOCUMENTS

| | | |
|---|---|---|
| DE | 3831540 A | 4/1989 |
| DE | 295 17 393 U1 | 3/1996 |
| EP | 0 280 564 | 8/1988 |
| GB | 2209678 | 5/1989 |
| JP | 60-203250 | 10/1985 |
| JP | 01-145066 | 6/1989 |

(List continued on next page.)

OTHER PUBLICATIONS

"Abstracts From the 68th Scientific Sessions, Anaheim Convention Center, Anaheim, California, Nov. 13–16, 1995", *American Heart Association Supplement to Circulation*, vol. 92, No. 8, Abstracts 1810–1813 (Oct. 15, 1995).
Capomolla et al., "Dobutamine and nitroprusside infusion in patients with severe congestive heart failure: Hemodynamic improvement by discordant effects on mitral regurgitation, left atrial function, and ventricular function", *American Heart Journal*, vol. 134, No. 6, pp. 1089–1098 (Dec. 1997).
Capouya et al., "Girdling Effect of Nonstimulated Cardiomyoplasty on Left Ventricular Function", *The Society of Thoracic Surgeons*, vol. 56, pp. 867–871 Dec. 1993.
Cohn, "The Management of Chronic Heart Failure", *The New England Journal of Medicine*, vol. 335, No. 7, pp. 490–498 (Aug. 15, 1996).

(List continued on next page.)

*Primary Examiner*—Samuel G. Gilbert
(74) *Attorney, Agent, or Firm*—Merchant & Gould P.C.

(57) ABSTRACT

A method and device are disclosed for treating congestive heart disease. The material of the device is secured to the heart proximate the septal wall. The material covering the ventricles may or may not have the same tension and or compliance. The device can be constructed as a unitary "jacket" that is slipped over the apex of the heart. Alternately, the device implanted as one, two or more separate components. In one embodiment, the material covers both the left and right ventricles. In another embodiment, the material covers only one ventricle. The device may include at least one adjustment mechanism configured to adjust the tension of the material. Preferably, the device includes a first adjustment mechanism configured to adjust a tension of the material covering the right ventricle and a second adjustment mechanism configured to adjust the tension of the material covering the left ventricle such that the tension of the material covering the left ventricle can be different than the tension of the material covering the right ventricle.

37 Claims, 10 Drawing Sheets

U.S. PATENT DOCUMENTS

| | | | |
|---|---|---|---|
| 4,821,723 A | | 4/1989 | Baker, Jr. et al. |
| 4,834,707 A | | 5/1989 | Evans |
| 4,878,890 A | | 11/1989 | Bilweis |
| 4,936,857 A | | 6/1990 | Kulik |
| 4,957,477 A | | 9/1990 | Lundback |
| 4,973,300 A | | 11/1990 | Wright |
| 4,976,730 A | | 12/1990 | Kwan-Gett |
| 5,057,117 A | | 10/1991 | Atweh |
| 5,087,243 A | | 2/1992 | Avitall |
| 5,131,905 A | | 7/1992 | Grooters |
| 5,150,706 A | | 9/1992 | Cox et al. |
| 5,186,711 A | | 2/1993 | Epstein |
| 5,192,314 A | | 3/1993 | Daskalakis |
| 5,256,132 A | | 10/1993 | Snyders |
| 5,290,217 A | | 3/1994 | Campos |
| 5,356,432 A | | 10/1994 | Rutkow et al. |
| 5,383,840 A | | 1/1995 | Heilman et al. |
| 5,385,156 A | | 1/1995 | Oliva |
| 5,429,584 A | | 7/1995 | Chiu |
| 5,507,779 A | | 4/1996 | Altman |
| 5,524,633 A | | 6/1996 | Heaven et al. |
| 5,603,337 A | | 2/1997 | Jarvik |
| 5,647,380 A | | 7/1997 | Campbell et al. |
| 5,702,343 A | | 12/1997 | Alferness |
| 5,713,954 A | | 2/1998 | Rosenberg et al. |
| 5,800,528 A | | 9/1998 | Lederman et al. |
| 6,077,214 A | * | 6/2000 | Mortier et al. .............. 128/898 |
| 6,174,279 B1 | * | 1/2001 | Girard ......................... 600/37 |
| 6,193,648 B1 | * | 2/2001 | Krueger ....................... 600/37 |
| 6,425,856 B1 | * | 7/2002 | Shapland et al. ............. 600/16 |
| 6,432,039 B1 | * | 8/2002 | Wardle ........................ 600/16 |

FOREIGN PATENT DOCUMENTS

| | | |
|---|---|---|
| SU | 1009457 | 4/1983 |
| WO | WO 98/29041 | 7/1998 |
| WO | WO 98/58598 | 12/1998 |
| WO | WO 99/44534 | 9/1999 |
| WO | WO 00/02500 A | 1/2000 |

OTHER PUBLICATIONS

Coletta et al., "Prognostic value of left ventricular volume response during dobutamine stress echocardiography", *European Heart Journal*, vol. 18, pp. 1599–1605 (Oct. 1997).

Kass et al., "Reverse Remodeling From Cardiomyoplasty in Human Heart Failure", *Circulation*, vol. 91, No. 9, pp. 2314–2318 (May 1, 1995).

Levin et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, "Two–Bar Fabrics (Part–Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, vol. 64 (1997).

Guasp, F., "A containment prosthesis for the surgical treatment of dilated cardiomyopathy," *Rev. Esp. Cardiol.*, vol. 51, No. 7, pp. 521–528 (1998). (This is the English translation of Spanish reference "Una protesis contentiva para el tratamiento de la miocardiopatia dilatada" cited in Information Disclosure Statement filed by Applicants on Dec. 22, 2000).

* cited by examiner

CARDIAC DISEASE TREATMENT AND DEVICE

BACKGROUND OF THE INVENTION

1. Field of the Invention

The present invention is directed to a method and device for treating congestive heart disease and related valvular dysfunction. More particularly, the invention provides a cardiac support device with sections having variable compliance.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly prescribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. Heart transplant procedures are very risky, extremely invasive and expensive and only shortly extend a patient's life. Furthermore, not enough hearts are available for transplant to meet the needs of congestive heart disease patients and many patient's do not qualify for heart transplant for failure to meet any one of a number of qualifying criteria.

Substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic support. The study suggests an elastic support (i.e., a non-stimulated muscle wrap or an artificial elastic sock placed around the heart) could provide similar benefits. Kass et al., *Reverse Remodeling From Cardiomyoplasty In Human Heart Failure: External Support Versus Active Assist,* 91 Circulation 2314–2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable support on the contraction of the heart during systole.

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of such is shown in U.S. Pat. No. 4,995,857 to Arnold dated Feb. 26, 1991. LVAD surgeries are still in U.S. clinical trials and not generally available. Such surgeries are expensive. The devices are at risk of mechanical failure and frequently require external power supplies. TAH devices, such as the celebrated Jarvik heart, are used as temporary measures while a patient awaits a donor heart for transplant.

Other attempts at cardiac assist devices are found in U.S. Pat. No. 4,957,477 to Lundbäck dated Sep. 18, 1990, U.S. Pat. No. 5,131,905 to Grooters dated Jul. 21, 1992 and U.S. Pat. No. 5,256,132 to Snyders dated Oct. 26, 1993. Both of the Grooters and Snyders patents teach cardiac assist devices which pump fluid into chambers opposing the heart to assist systolic contractions of the heart. The Lundbäck patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

Commonly assigned U.S. Pat. No. 5,702,343 to Alferness dated Dec. 30, 1997 teaches a jacket to constrain cardiac expansion during diastole. The present invention pertains to improvements to the invention disclosed in the '343 patent.

SUMMARY OF THE INVENTION

According to a preferred embodiment of the present invention, a method and device are disclosed for treating congestive heart disease and related cardiac complications such as valvular disorders. The invention includes a device constructed from biologically compatible material dimensioned to cover at least one ventricle of the heart. The device is adapted to be secured to the heart and is adjustable to snugly conform to an external geometry of the heart and assume a maximum adjusted volume for the jacket to constrain circumferential expansion of the heart beyond the maximum adjusted volume during diastole and to permit unimpeded contraction of the heart during systole.

In particular, the invention provides a device constructed such that material covering one ventricle can have a different a compliance or tension than material covering the other ventricle. In a preferred embodiment, the material of the device is secured to the heart proximate the septal wall.

The device can be constructed as a unitary "jacket" that is slipped over the apex of the heart (See, for example, U.S. Pat. No. 5,702,343 to Alferness, dated Dec. 30, 1997, the disclosure of which is incorporated by reference herein). Alternately, the device may be implanted as two or more separate components (pieces of material). In one embodiment, the device covers both the left and right ventricles. In another embodiment, the device covers only the left ventricle or only the right ventricle.

Preferably, the device includes at least one adjustment mechanism configured to adjust the tension of the material. More preferably, the device includes a first adjustment mechanism configured to adjust a tension of the material covering the right ventricle and a second adjustment mechanism configured to adjust the tension of the material covering the left ventricle such that the tension of the material covering the left ventricle can be different than the tension of the material covering the right ventricle.

The invention also provides a method for implanting the device, both as a unitary device, or as multiple components.

DESCRIPTION OF THE PREFERRED EMBODIMENT

Healthy Human Heart

Figure 1:
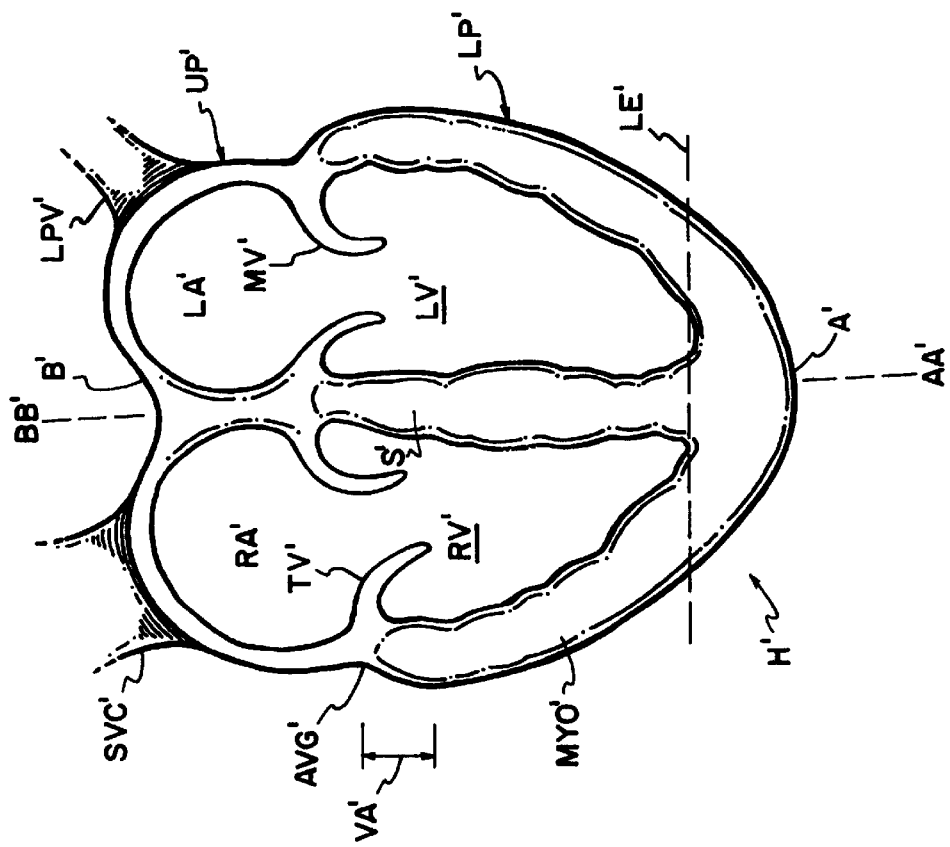
FIG. 1 is a schematic cross-sectional view of a normal, healthy human heart shown during systole.
Figure 1A:
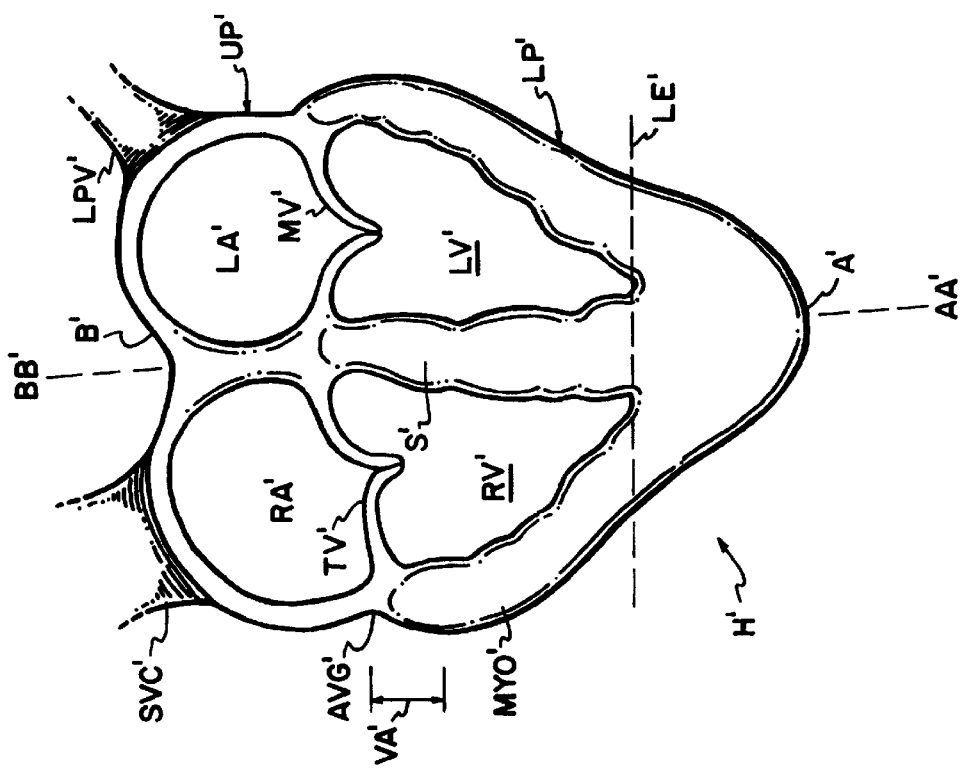
FIG. 1A is the view of FIG. 1 showing the heart during diastole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The plane in which the valves separating the atria and ventricles lie is visible from the exterior of the heart H' and is designated as the valvular annulus VA'. The heart H' has a length measured along a longitudinal axis AA'-BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

The right and left atria RA' and LA' receive blood from the venous system and the right and left ventricles RV' and LV' pump blood into the arterial system. The right atrium and ventricle RA' and RV' are separated from the left atrium and ventricle LA' and LV' by a muscular wall, or septum S'.

Blood in which the oxygen content has become partially depleted and the carbon dioxide content has increased as a result of tissue metabolism returns to the right atrium RA'. This blood then enters the right ventricle RV', which pumps it into the pulmonary arteries. The pulmonary arteries branch to transport blood to the lungs. The blood that returns to the left atrium LA' by way of the pulmonary veins LPV' is therefore enriched in oxygen. The path of blood from the heart (right ventricle RV') through the lungs; and back to the heart (left atrium LA') is referred to as pulmonary circulation.

Oxygen rich blood in the left atrium LA' enters the left ventricle LV' and is pumped into the aorta. Arterial branches from the aorta supply oxygen rich blood to all of the organ systems and are thus part of the systemic circulation.

Arterial pressure is significantly higher in the systemic circulation than in the pulmonary circulation. Therefore the left ventricle LV' performs more work than the right ventricle RV'. As a result, in healthy hearts, the left ventricle LV' wall is generally about twice as thick as that of the right ventricle RV'.

The Cardiac Cycle

The events that occur from the beginning of one heartbeat to the beginning of the next are referred to as the cardiac cycle. Generally, the cardiac cycle includes a period of relaxation called diastole, during which blood flows from the veins into the atria and ventricles, followed by a period of contraction called systole. FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H'. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

During the initial segment of diastole, blood flows from the veins, directly through the atria and into the ventricles. During the final segment of diastole, the atria contract, causing additional filling of the ventricles. In a typical human heart, the right atrial pressure rises to about 4 to about 6 mmHg during atrial contraction. In contrast, the left atrial pressure rises to about 7 to about 8 mmHg during atrial contraction.

Immediately after ventricular contraction begins, the ventricular pressure abruptly rises, causing the A-V valves to close. The ventricular pressure then builds up sufficiently to push the semilunar (aortic and pulmonary) valves open against the pressures in the aorta and pulmonary artery. The ventricular pressures push the semilunar valves open when the left ventricular pressure rises above diastolic aortic pressure, to between about 80 mmHg to 85 mmHg, (and the right ventricular pressure rises above pulmonary artery diastolic pressure, to between about 8 mmHg and 10 mmHg). At the end of systole, ventricular relaxation begins suddenly, allowing the intraventricular pressures to fall rapidly. The elevated pressures in the distended large arteries immediately push blood back toward the ventricles, which snaps the aortic and pulmonary valves closed. The ventricular muscle continues to relax and the intraventricular pressures fall rapidly back to their low diastolic levels. Then the AV valves open to begin a new cycle.

Comparison of a Diseased Heart and a Healthy Heart

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
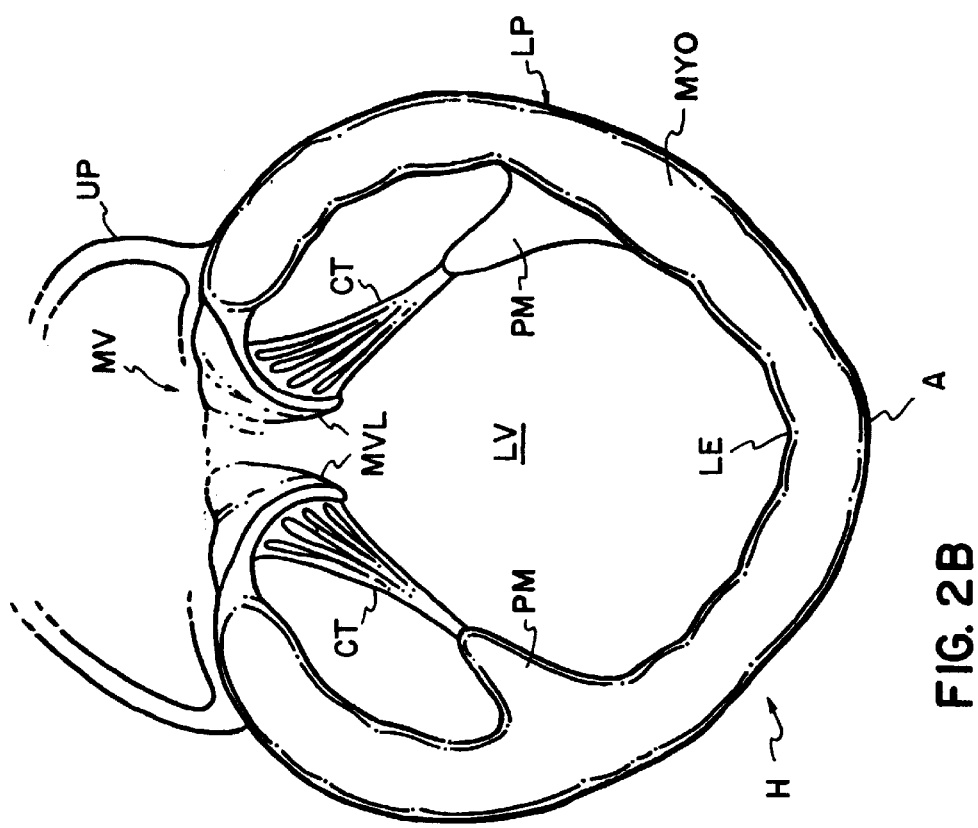
FIG. 2B is the view of FIG. 1B showing a diseased heart.
Figure 2A:
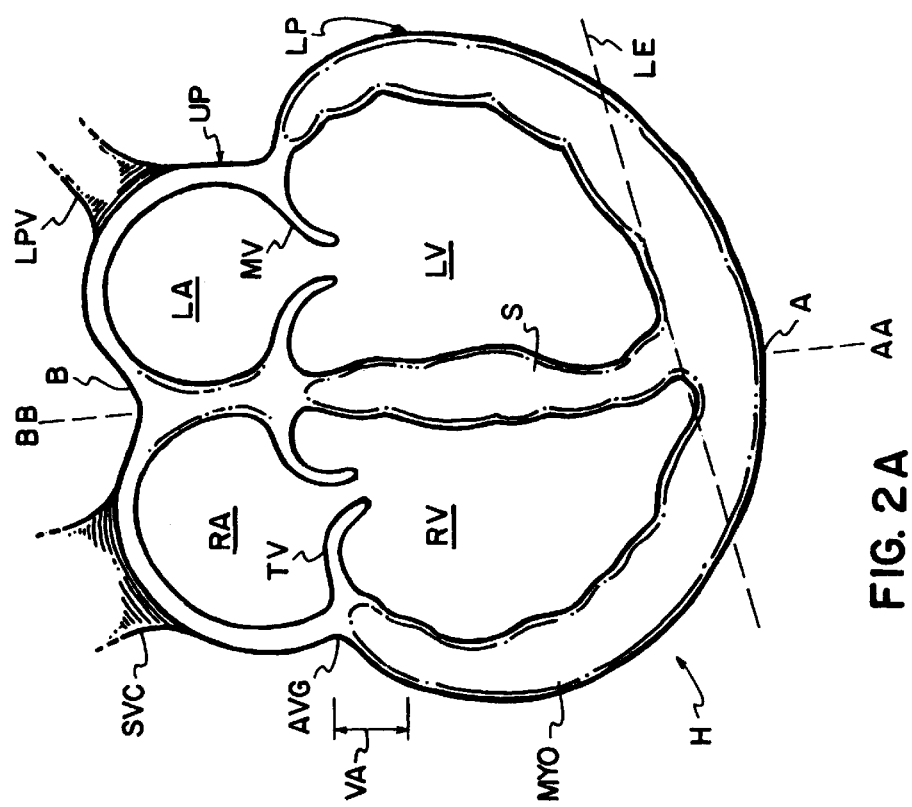
FIG. 2A is the view of FIG. 2 showing the heart during diastole.
Figure 2:
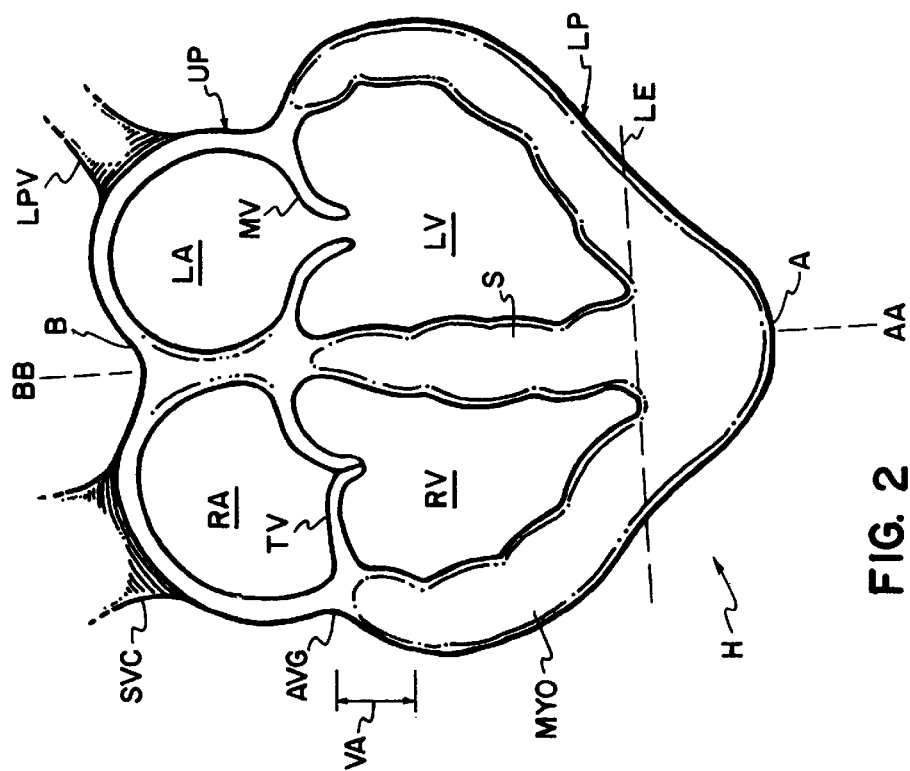
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
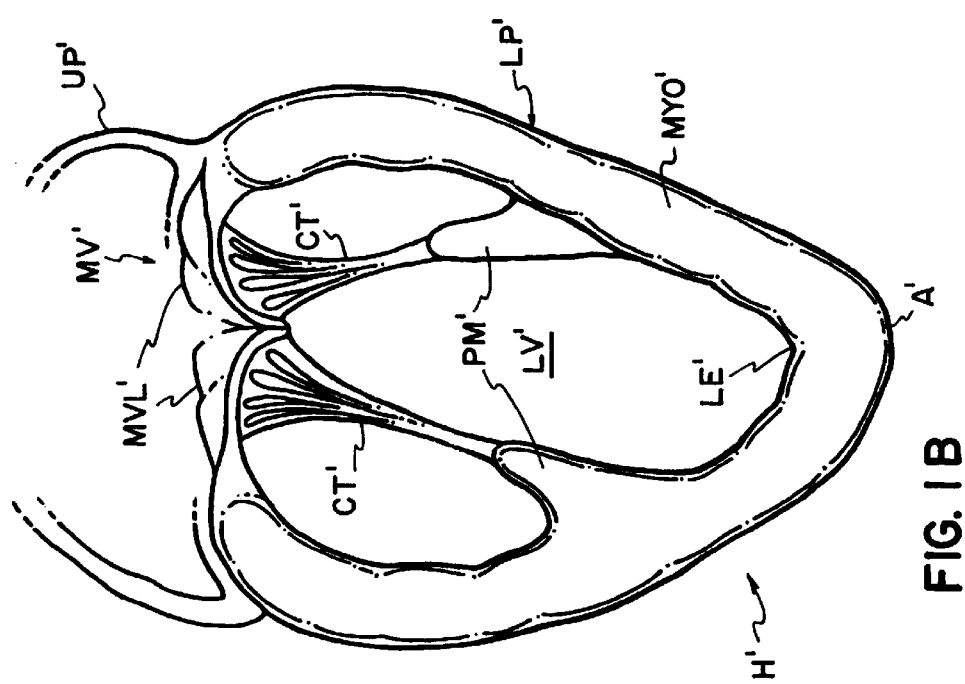
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

Cardiac Support Device

In general, the invention provides a cardiac support device configured to cover at least the left or right ventricular myocardium to constrain against enlargement of the ventricular wall of the heart H without restricting contraction of the heart H during systole.

As used herein, "cover" means that the device is in contact with the cardiac surface and reduces expansion of the heart wall during diastole by applying a constraining force on the surface of the heart. A device that "covers" the lower extremities of the heart may be constructed as a continuous material that can substantially encircle the external surface of the lower extremities of the heart. In an alternate embodiment, the device is constructed as one or two or more separate components. In, one embodiment, the device is constructed from at least one component configured to substantially overly one ventricle of the heart (e.g., extend from septal wall to septal wall). Alternately, the device may be constructed from one or more components, each of which overly only a segment or piece of a ventricle.

The device 10 is adjusted to a snug fit on the heart H during diastole. Care is taken to avoid tightening the device 10 too much such that cardiac function is impaired. During diastole, the ventricles fill with blood. If the device 10 is too tight, the ventricles may not adequately expand. During the fitting of the device 10, the surgeon can monitor ventricular pressure, for example, by monitoring pulmonary wedge pressure. While minor increases in pressure (e.g., 2–3 mmHg) can be tolerated, the device 10 is snugly fit on the heart H but not so tight as to cause a significant increase in left ventricular pressure during diastole.

Figure 3A:
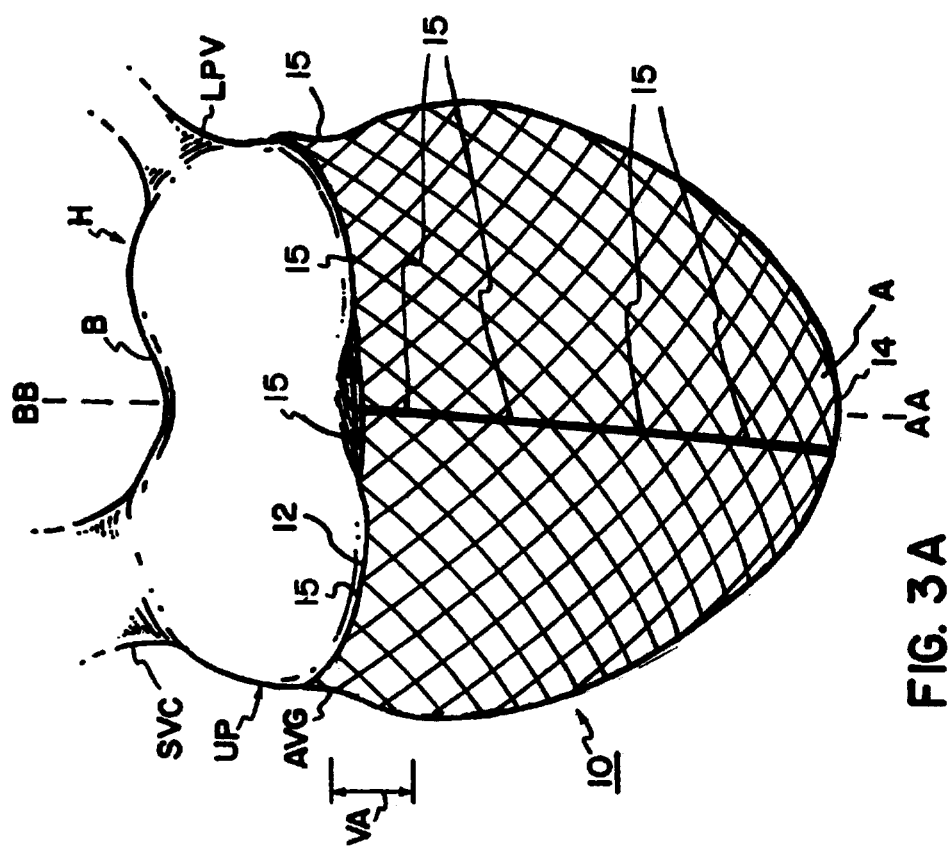
FIG. 3A is a side elevation view of a diseased heart in diastole with the device of FIG. 3 in place.
Figure 3:
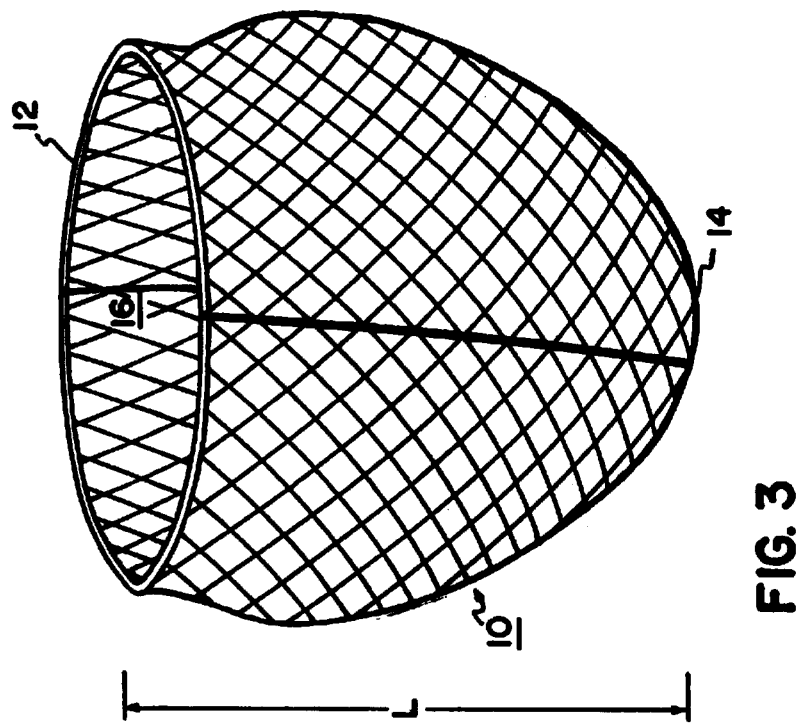
FIG. 3 is a perspective view of a first embodiment of a cardiac support device according to the present invention.
Figure 4A:
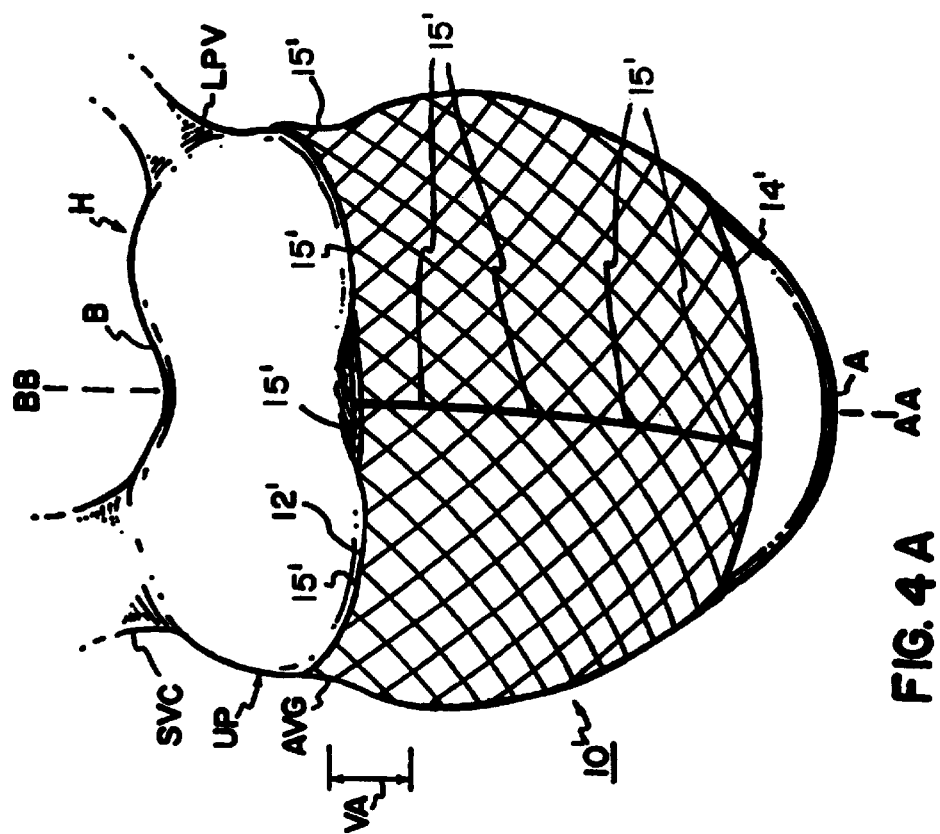
FIG. 4A is a side elevation view of a diseased heart in diastole with the device of FIG. 4 in place.
Figure 4:
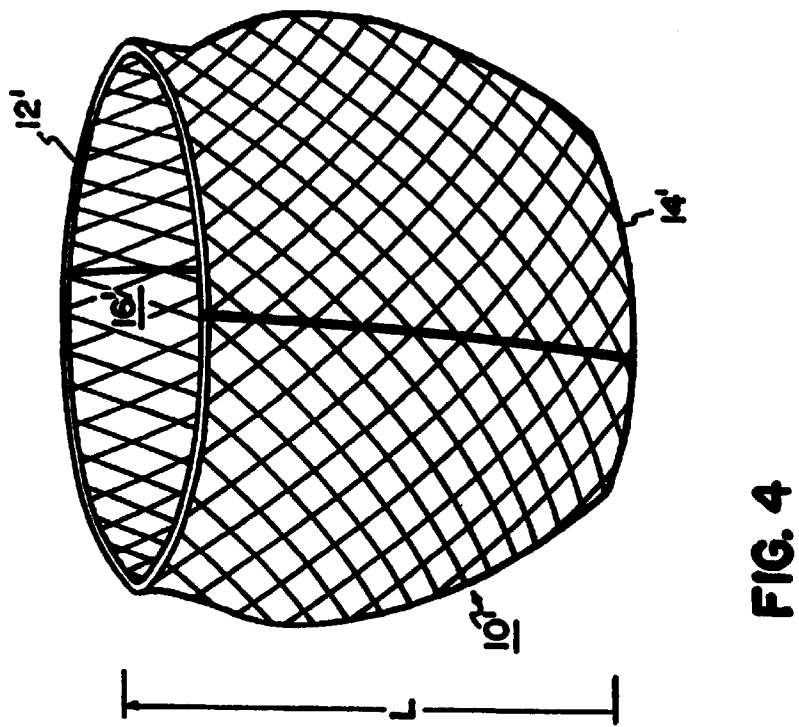
FIG. 4 is a perspective view of a second embodiment of a cardiac support device according to the present invention.

With reference now to FIGS. 3, 3A, 4 and 4A, the device of the present invention is shown to include flexible, biologically compatible material. The device 10 is generally a knit material having upper and lower ends 12, 14. In one embodiment, the device 10, 10' defines an internal volume 16, 16' which is completely enclosed but for the open ends 12, 12' and 14'. In the embodiment of FIG. 3, lower end 14 the device encloses the apex of the heart. In the embodiment of FIG. 4, lower end 14' is open, i.e., the apex of the heart protrudes beyond the lower end 14' of the device. In both embodiments, upper ends 12, 12' are open. Elements in common between the figures are numbered identically with the occasional addition of an apostrophe to distinguish one embodiment from another. Such elements need not be separately discussed.

The device 10 is dimensioned with respect to a heart H to be treated. Specifically, the device 10 is sized for expansion of the heart H to be constrained. The device 10 has a length L between the upper and lower ends 12, 14 sufficient for the device 10 to constrain the left or right (or both) ventricular lower extremities of the heart H. The upper end 12 of the jacket 10 extends up to, and if desired, to include, the valvular annulus VA. Where it is desired to constrain enlargement of the upper portion UP, the device 10 may be extended to cover the upper portion UP. In a preferred embodiment, the device 10 is sized so that the upper end 12 can reside in the A-V groove AVG.

Sizing the device 10 for the upper end 12 to terminate at the A-V groove AVG is desirable for a number of reasons. First, the groove AVG is a readily identifiable anatomical feature to assist a surgeon in placing the device 10. By placing the upper end 12 in the A-V groove AVG, the surgeon is assured the device 10 will provide sufficient support at the valvular annulus VA. The A-V groove AVG and the major vessels act as natural stops for placement of the device 10 while assuring coverage of the valvular annulus VA. Using such features as natural stops is particularly beneficial in minimally invasive surgeries where a surgeon's vision may be obscured or limited.

After the device 10 is positioned on the heart H as described above, the device 10 is secured to the heart. Preferably, the device 10 is secured to the heart H through sutures. The device 10 is sutured to the heart H at suture locations 15 circumferentially spaced along the upper end 12 and along or proximate the septal wall.

Figure 5:
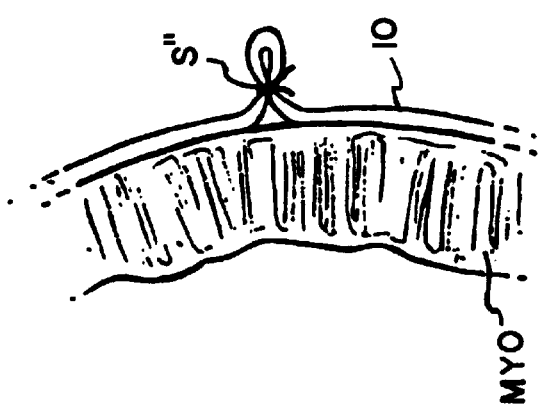
FIG. 5 is a cross-sectional view of a device of the present invention overlying a myocardium and with the material of the device gathered for a snug fit.

To permit the device 10 to be easily placed on the heart H, the material of the device 10 is preferably larger than the lower portion LP of the heart H during diastole. So sized, the device 10 may be easily applied to the heart H. Once secured, the device 10 may be adjusted to snugly conform to the external geometry of the heart H during diastole. Such sizing is easily accomplished due to the knit construction of the device 10. For example, excess material of the jacket 10 can be gathered and sutured S" (FIG. 5) to reduce the maximum diastolic volume and conform the material to the shape of the heart H during diastole. As an alternative to gathering the material, the tension of the material can be adjusted using other methods discussed below.

Variable Compliance

The device 10 described above is configured to surround at least parts of the left and/or right ventricular chambers to provide support at end diastole to reduce dilation associated with heart failure. According to one embodiment of the invention, the device 10 may be constructed such that pressure exerted by the device on one ventricle is different than the pressure exerted by the device on the other ventricle.

In a preferred embodiment, the device 10 of the present invention takes into consideration the physiological differences between the right and left ventricles RV and LV (i.e., the right ventricular wall is generally about half the thickness of the left ventricular wall and the pressure in the right ventricle is substantially lower than that of the left ventricle). Because excess pressure on the right ventricle RV may prevent filling of the right ventricle RV, the pressure exerted by the device on the right ventricle RV is preferably less than the end diastolic pressure of the right ventricle RV.

Generally, the end diastolic pressure of the left ventricle is higher than the end diastolic pressure of the right ventricle. For example, in a healthy heart, the end diastolic pressure of the left ventricle is between about 6 mmHg and about 8 mmHg whereas the end diastolic pressure of the right ventricle is between about 4 mmHg and about 6 mmHg. Generally, in a healthy heart, the end systolic pressure of the left ventricle is between about 100 mmHg and about 120 mmHg and the end systolic pressure of the right ventricle is between about 18 mmHg and about 24 mmHg. Generally, the end diastolic in both the right and left ventricle and atria are higher in a diseased heart H than in a healthy heart H'.

The invention provides a device 10 in which the pressure exerted by the device 10 on the right ventricle RV may be different (i.e., less) than the pressure exerted by the device 10 on the left ventricle LV. Preferably the pressure differential is feasibly because the material of the device 10 is secured to the cardiac surface. Although the material can be secured anywhere on the cardiac surface, the material is preferably secured at a location at or proximate the septal wall that separates the two ventricles. Preferably, the material is secured via sutures that extend through the myocardium, preferably the suture extend through the ventricle wall.

Attachment of the material to the cardiac surface helps disconnect the applied ventricular pressure and tension in the material covering each ventricle such that the right ventricle and left ventricle can.achieve different diastolic pressures. Because the left ventricle typically expands at a higher pressure than the right ventricle, a cardiac support device (which defines a specific volume) implanted without attachment to the cardiac surface (i.e., proximate the septal wall) may result in left ventricle filling at the expense of right ventricle expansion. Such as "volume shift" could occur even with a device constructed wherein the material configured to cover the right ventricle has a different compliance than the material configured to cover the left ventricle. However, a cardiac support device constructed wherein the material designed to cover the right ventricle has a different compliance than the material designed to cover the left ventricle is implanted without septal attachment may still be desirable. Although such an embodiment may not initially address the "volume shift" phenomenon, once fibrosis secures the material in place on the cardiac surface, the differing compliance in the fabric would allow different filling profiles for each ventricle.

The device may be installed as a single unitary "jacket" configured to cover both the right and left ventricles or as one or two or more separate components (e.g., a first component configured to cover the right ventricle and a second component configured to cover the left ventricle). Generally, for a unitary device, a conical jacket is first positioned over the heart. At this time it may be desirable to anchor the device in a few locations around the base of the heart. The device is then secured to the heart, preferably proximate the septal line. Once secured to the heart, the tension of the material covering each ventricle may be adjusted. The tension of the material covering the right ventricle can be lower than the tension of the material covering the left, if desired. If desired, the device can be further anchored by placing additional sutures at the base.

Figure 10:
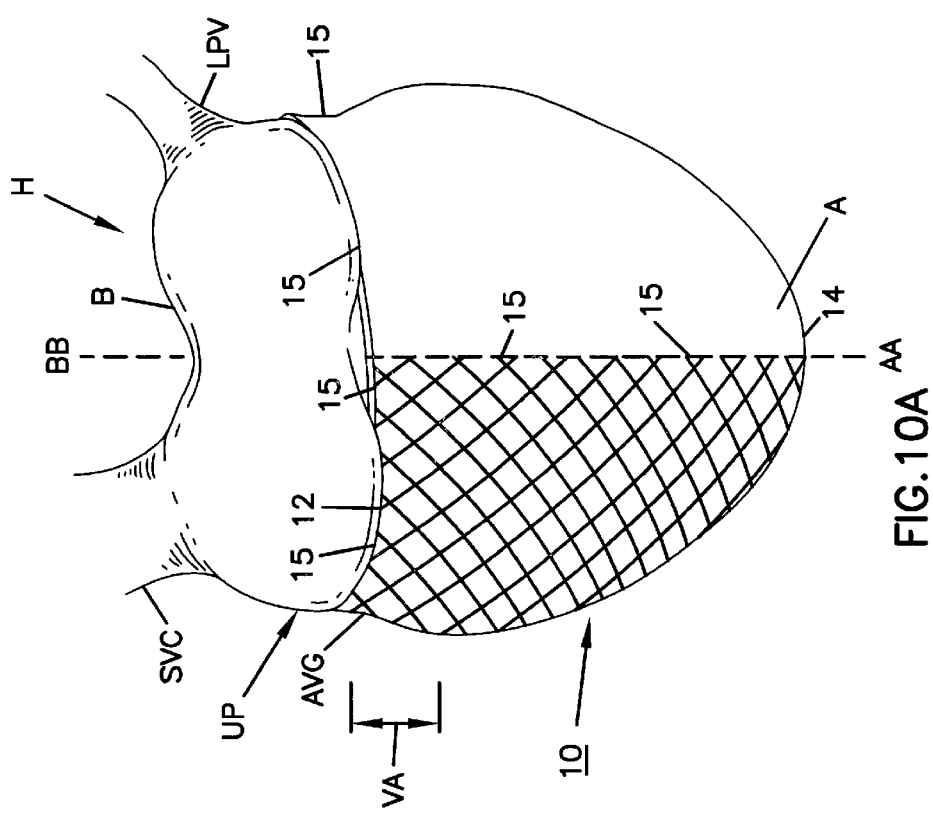
FIG. 10 is a side elevation view of an embodiment of a cardiac support device covering only the left ventricle according to the present invention.
Figure 10A:
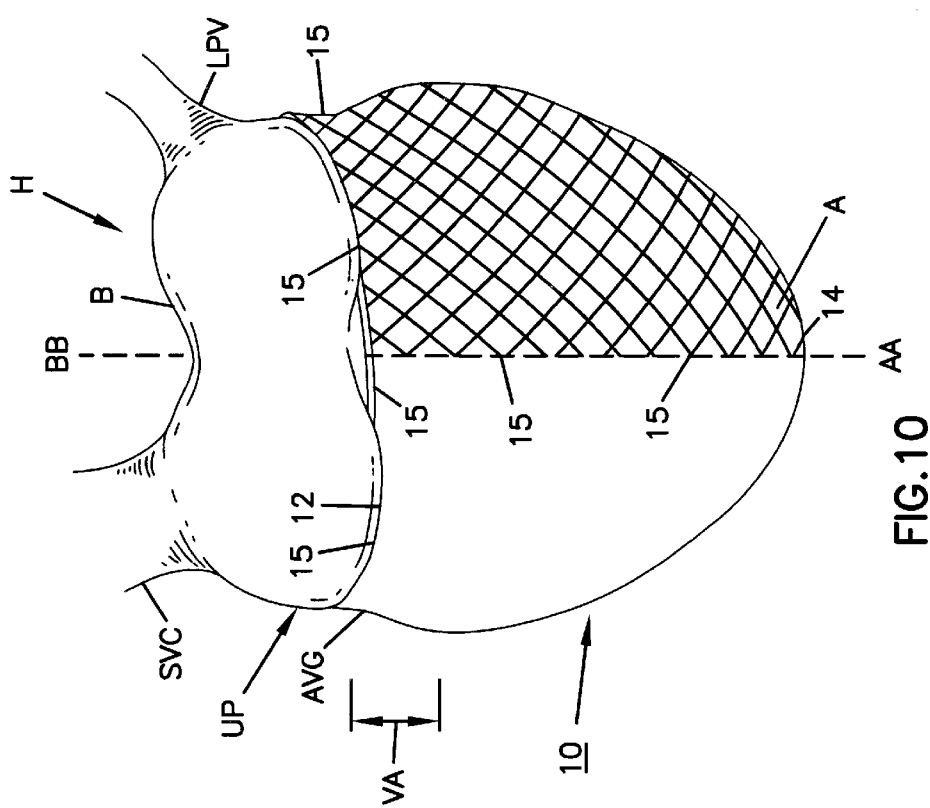
FIG. 10a is a side elevation view of another embodiment of a cardiac support device covering only the right ventricle according to the present invention.

Alternately, the device can be installed as two or more separate components. According to one embodiment, a first component (e.g., a piece of material) having a preselected size is positioned over a first ventricle. Lateral edges of the material are attached to the cardiac surface, preferably by sutures that extend through the myocardium, most preferably at or proximate the septal wall. The top and bottom of the material are also sutured to the cardiac surface. If desired, a second component (e.g., a second piece of material) having a preselected size may be positioned over the remaining ventricle and secured in a similar manner. In one embodiment, the device may be implanted only over left ventricle, leaving the right ventricle unrestricted, for example, to constrain left ventricular expansion (FIG. 10). Alternately, it may be desirable to constrain the expansion of only the right ventricle, for example, an infarcted right ventricle RV' to prevent aneurysm of the right side, while not restraining the left ventricle LV' (e.g., if the left ventricle is healthy) (FIG. 10a). In a further embodiment, the device may comprise a plurality of components. For example, one ventricle (right or left, or both) may be covered with one or more pieces of material, each having the same or different compliance.

Figure 8A:
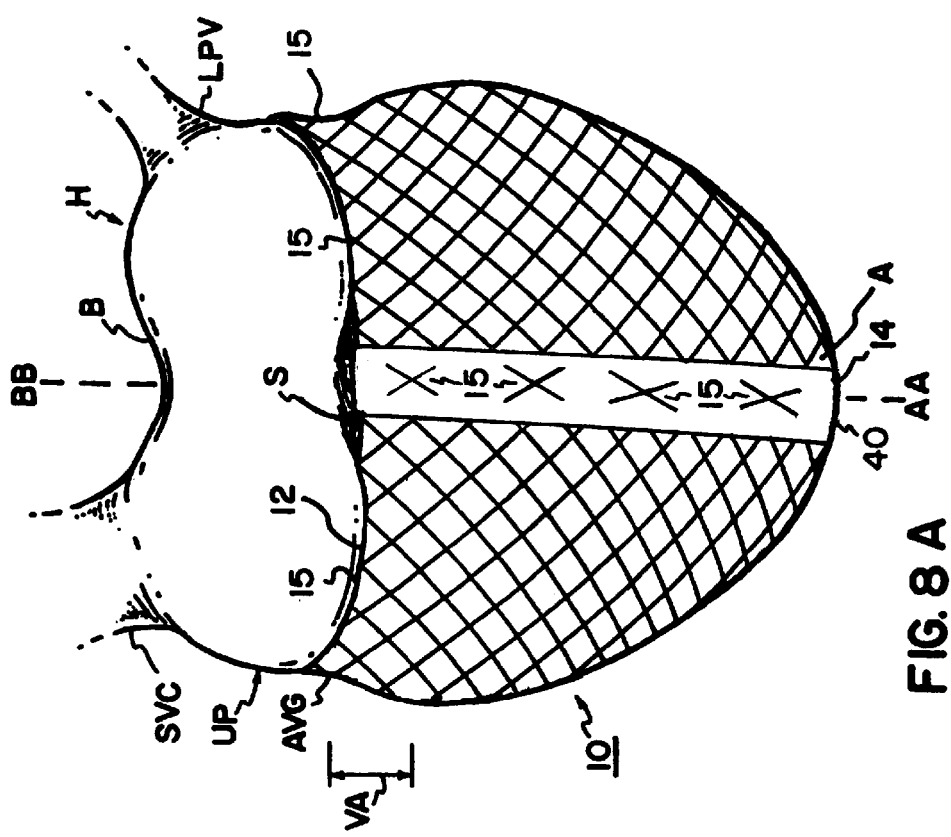
FIG. 8A is a side elevation view of a diseased heart in diastole with the device of FIG. 8 in place.
Figure 8:
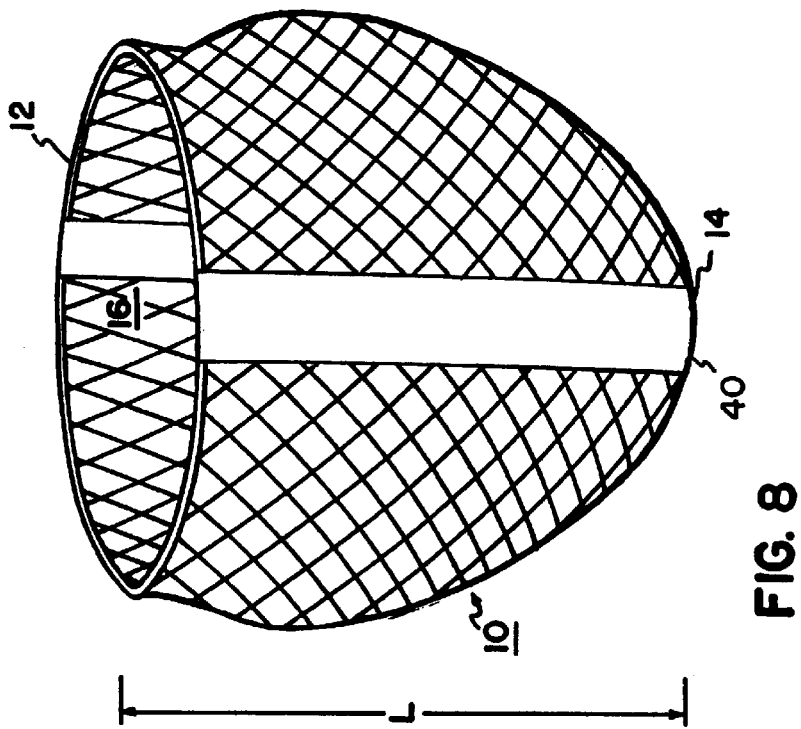
FIG. 8 is a perspective view of an alternate embodiment of a cardiac support device according to the present invention.
Figure 9A:
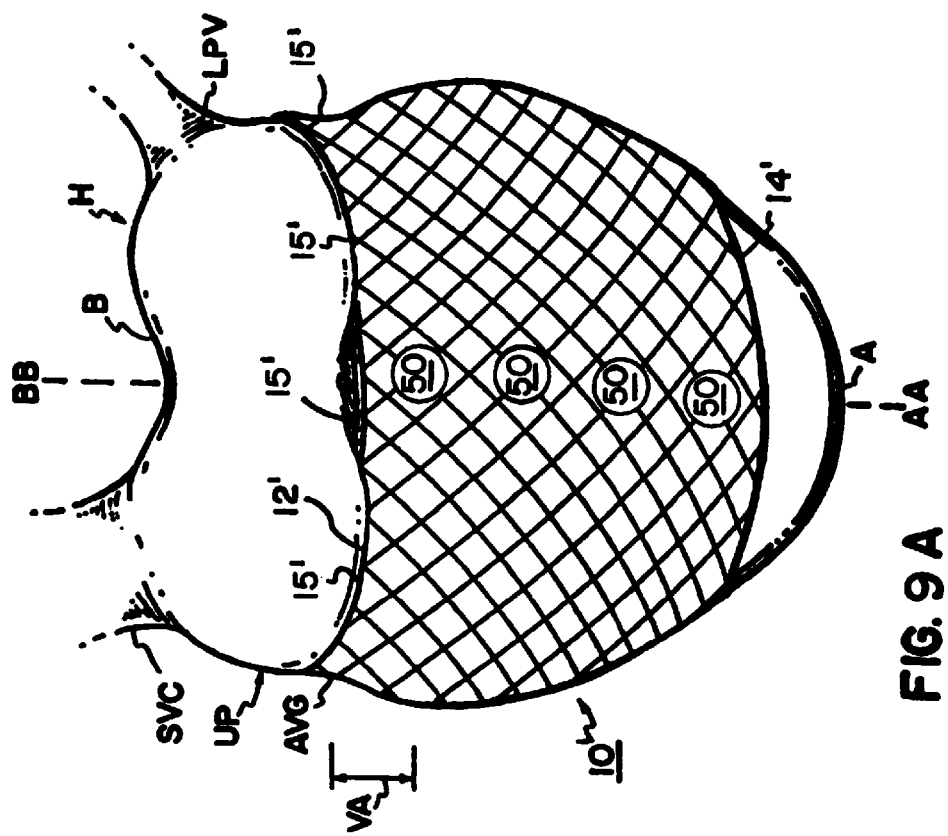
FIG. 9A is a side elevation view of a diseased heart with an alternate embodiment of a variable compliance device of FIG. 9 in place.
Figure 9:
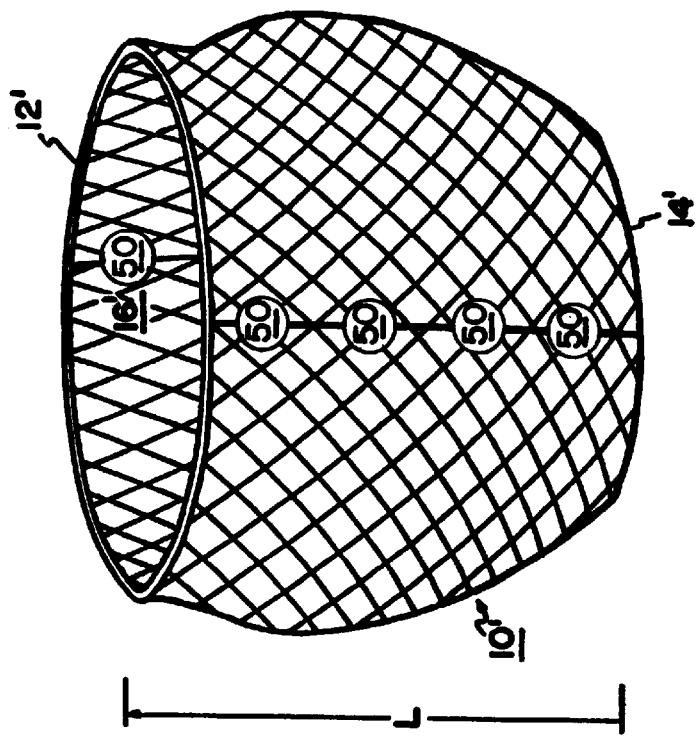
FIG. 9 is a perspective view of another embodiment of a cardiac support device according to the present invention.

The device 10 can be secured to the septal wall, or proximate the septal wall, using a variety of methods, including sutures, staples and adhesives. Actual attachment may be into or through the septal wall S' or into or through the left ventricle LV' near the septum. Typically, the device 10 is secured to the septal wall using sutures. In one embodiment, the knit material of the device 10 is sutured directly to the septal wall S'. (See FIGS. 3A and 4A) Alternately, the knit material of the device 10 may be secured to a securing member that is then secured to the septal wall. In one embodiment, the securing member is an inelastic band 40 that is secured to the septal wall (See FIG. 8A). In another embodiment, the knit material of the device 10 is secured to rings 50 of a material, for example, plastic, metal or fabric rings 50, wherein the rings 50 are then secured to the setpal wall (See FIG. 9A).

The pressure differential between the material covering the right and left ventricles can be achieved in a variety of ways. In one embodiment of the invention, the pressure differential is achieved by constructing the device using two types of material, one with a higher compliance than the other. A first piece of material is secured along or proximate the septal wall to cover one ventricle and a second piece of material is secured along or proximate the septal wall to cover a second ventricle.

According to one embodiment, the material covering the right ventricle RV is more compliant than the material covering the left ventricle LV. As used herein, the term "compliant" refers to a material that can expand in response to a force. "Compliance" refers to the displacement (in inches or centimeters) or strain (inches/inch or cm/cm) per a unit load (in pounds or kilograms) or load per unit width (in pounds per inch or kilograms per centimeter) for a material. A material that is more compliant is displaced further per unit load than a material that is less compliant. The compliance of the material may be due to a variety of factors, including, but not limited to, the compliance of the individual filaments 30 that make up the fibers 20, the relative movement of the filaments 30 within a fiber 20, and/or the relative movement of the intertwined fibers 20 when subjected to load. (See FIG. 6)

In one embodiment of the invention, the material covering the right ventricle is more compliant than the material covering the left ventricle. For example, the multiaxial expansion of the material covering the right ventricle may be between about 20% and 30% when exposed to a load between about 1 pounds per inch (1.8 N/cm) and about 3 pounds per inch (5 N/cm) whereas the material covering the left ventricle may have a multiaxial expansion between about 10% and 20% when exposed to the same load. The term "multiaxial expansion" refers expansion of a material along at least a first and a second axis and includes expansion along more than two axes.

In another embodiment, the pressure differential is achieved by having the tension of the material covering the left ventricle LV greater than the tension of the material covering the right ventricle RV. The tension of the material can be modified using a variety of methods. In one embodiment, various sized materials are prepared such that different sized pieces of material are used for different predetermined cardiac expansion sizes or expansion ranges. "Predetermined size" refers to the predetermined expansion limit of the material that circumferentially constrains cardiac expansion during diastolic filling of the heart.

Alternately, the material can include a mechanism for selectively adjusting the size of the material. Advantageously, such an adjustment mechanism can be used initially to set the tension of the material covering each ventricle, and also subsequently to readjust the amount of cardiac reinforcement as therapeutic reduction of cardiac expansion occurs. In one embodiment, the material covering one or both of the ventricles can be gathered and secured, for example, by suturing. (See FIG. 5)

According to another embodiment, an inflatable member is mounted between the material covering one of the ventricles and the epicardium. A separate inflatable member can be mounted between the material covering the other ventricle if desired. Alternately, an inflatable member may only be mounted between the material covering one ventricle and the ventricular epicardium. Inflating the inflatable member through an inflation port with, for example, a gas or a liquid can increase the tension of the material. Inflation of the inflatable member provides an increase in the tension of the material covering the ventricle.

Another mechanism for selectively adjusting the tension of the material can include a slot that opens at the base of the jacket and extends towards the apex. The slot includes opposing lateral edges. By adjusting the proximity of the opposing lateral edges, the tension of the material can be varied. Moving the opposing edges of the slot closer together narrows the slot and increases the material tension. The opposing edges of the slot can be fastened together at a predetermined proximity by, for example, one or more lateral attachment devices, such as a cord, suture, band, adhesive or shape memory element attached to each lateral edge.

Material

Figure 6:
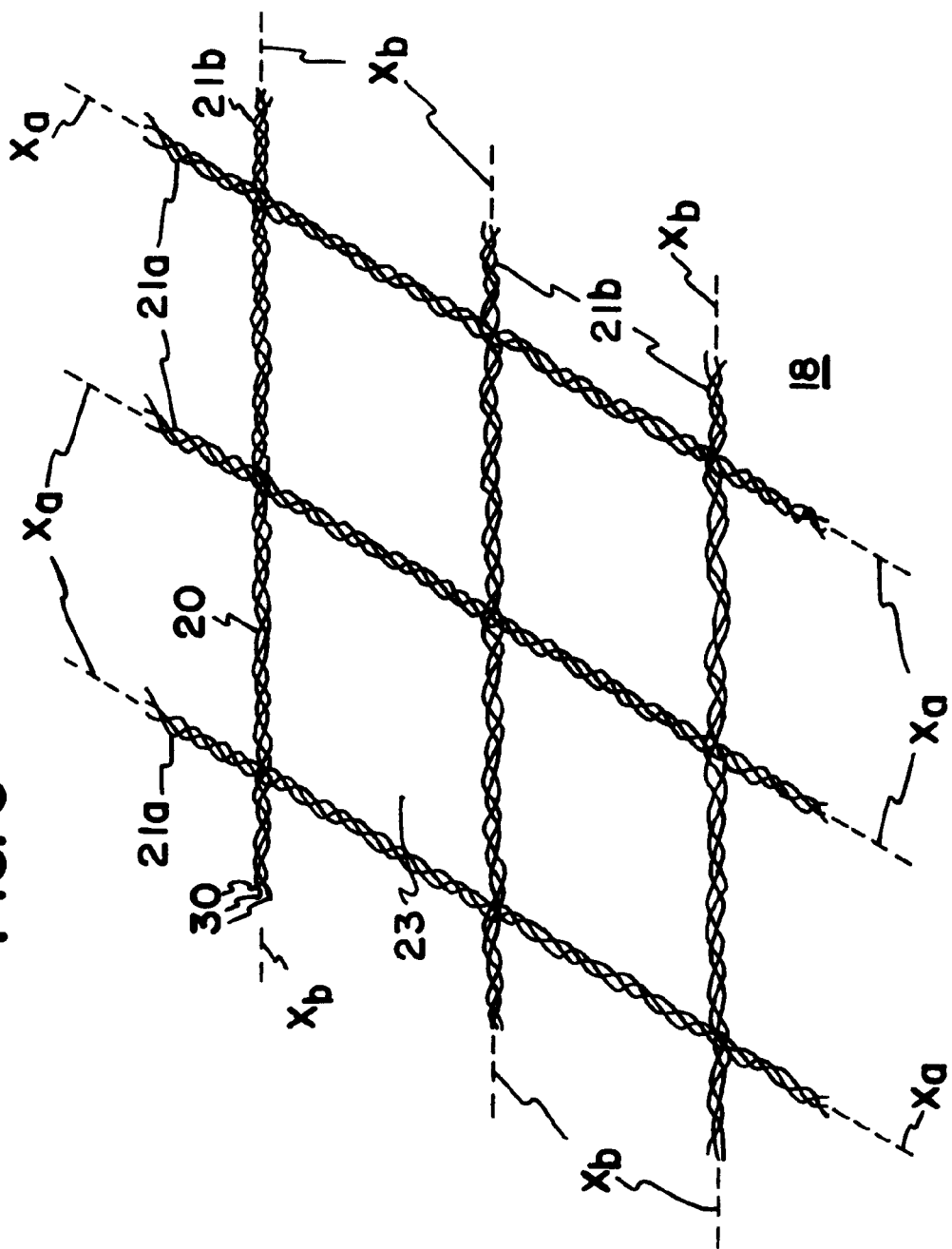
FIG. 6 is an enlarged view of a knit construction of the device of the present invention in a rest state.

As mentioned, the jacket 10 is constructed from a knit, biocompatible material. The knit 18 is illustrated in FIG. 6. Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state. FIG. 6 illustrates the knit 18 in a rest state. The fibers 20 of the fabric 18 are woven into two sets of fiber strands 21a, 21b having longitudinal axes $X_a$ and $X_b$. The strands 21a, 21b are interwoven to form the fabric 18 with strands 21a generally parallel and spaced-apart and with strands 21b generally parallel and spaced-apart.

Figure 7:
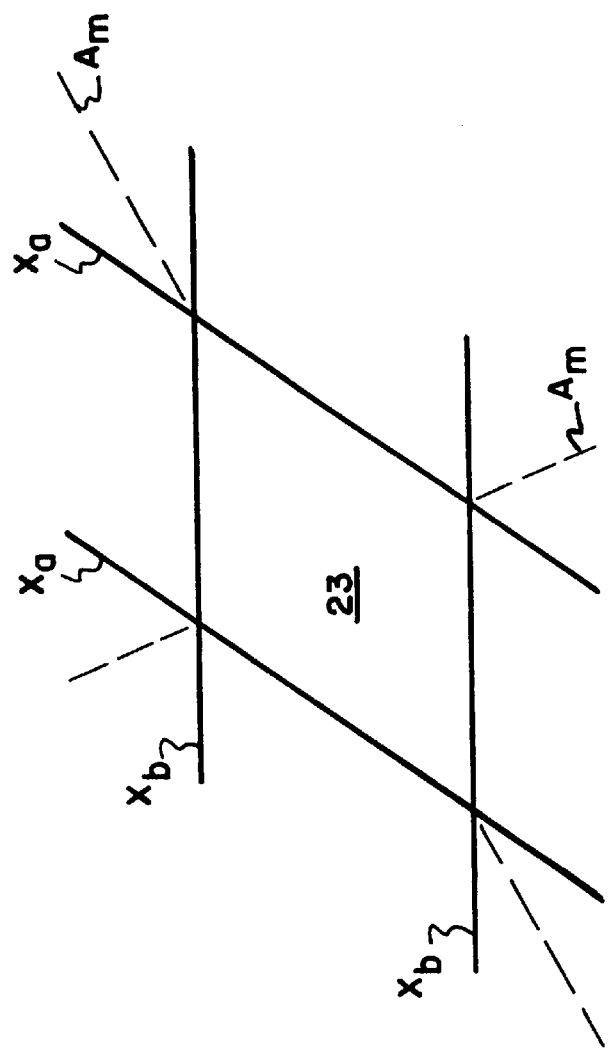
FIG. 7 is a schematic view of the material of FIG. 6.

For ease of illustration, fabric 18 is schematically shown in FIG. 7 with the axis of the strands 21a, 21b only being shown. The strands 21a, 21b are interwoven with the axes Xa and Xb defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA-BB While the jacket 10 is expandable due to the above described knit pattern, the fibers 20 of the knit 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE), polypropylene and stainless steel.

The knit material has numerous advantages. Such a material is flexible to permit unrestricted movement of the heart H (other than the desired support on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. Preferably, a maximum cell area is no greater than about 9 mm$^2$ (about 3 mm by 3 mm) and, more preferably, is about 5.8 mm$^2$ (about 2.4 mm by 2.4 cm). The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

With the foregoing, a device and method have been taught to treat cardiac disease. The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 is low-cost, easy to place and secure, and is susceptible to use in minimally invasive procedures. The thin, flexible fabric 18 permits the jacket 10 to be collapsed and passed through a small diameter tube in a minimally invasive procedure.

The jacket 10 can be used in early stages of congestive heart disease. For patients facing heart enlargement due to viral infection, the jacket 10 permits support of the heart H for a sufficient time to permit the viral infection to pass. In addition to preventing further heart enlargement, the jacket 10 treats valvular disorders by constraining circumferential enlargement of the valvular annulus and deformation of the ventricular walls.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). The material of the jacket 10 is uniformly thin (less than 1 mm thick). The thin wall construction is less susceptible to fibrosis and minimizes interference with cardiac contractile function.

In addition to the foregoing, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs (e.g., dobutamine, dopamine or epinephrine or any other positive inotropic agents) to reduce the heart size. The jacket of the present invention is then snugly placed on the reduced sized heart and prevents enlargement beyond the reduced size.

From the foregoing, a low cost, reduced risk method and device are taught to treat cardiac disease. The invention is adapted for use with both early and later stage congestive heart disease patients. The invention reduces the enlargement rate of the heart as well as reducing cardiac valve regurgitation.

What is claimed is:

1. A device for treating cardiac disease of a heart having a longitudinal axis from an apex to a base, an upper portion and a lower portion divided by an A-V groove, a valvular annulus adjacent said A-V groove, and ventricular lower extremities adjacent said apex, said ventricular lower extremities comprising a right ventricle and left ventricle wherein said right and left ventricle are separated by a septum, the device comprising:
    a first component comprising a flexible material configured to cover said left ventricle and a second component comprising material configured to cover said right ventricle, wherein said first and second components are implanted separate;
    said material adapted to be adjusted on said heart to snugly conform to an external geometry of said heart and constrain circumferential expansion of at least said left ventricle or at least said right ventricle during diastole and permit substantially unimpeded contraction of said heart during systole, wherein pressure exerted by said device on said right ventricle during diastole is different than pressure exerted by said device on said left ventricle during diastole.

2. The device of claim 1, wherein said material is adapted to be secured to said heart proximate said septum.

3. The device of claim 1, wherein said material is secured to said heart by fibrosis.

4. The device of claim 1, wherein said material covering said right ventricle has a greater compliance than said material covering said left ventricle.

5. The device of claim 1, wherein said material covering said left ventricle is under more tension than said material covering said right ventricle.

6. The device of claim 1, further comprising a first adjustment mechanism configured to adjust a tension of said material covering said right ventricle and a second adjustment mechanism configured to adjust a tension of said material covering said left ventricle, wherein the tension of the material covering said left ventricle is greater than the tension of the material covering said right ventricle.

7. The device of claim 1, further comprising at least one adjustment mechanism configured to adjust a tension of said material.

8. The device of claim 7, wherein said adjustment mechanism comprises material that is sufficiently flexible such that excess amounts of said material can be gathered following placement of said material over said heart to snugly conform said material to an external geometry of said heart.

9. The device of claim 7, wherein said adjustment mechanism comprises a slot comprising opposing lateral edges, wherein the tension of said material is adjusted by adjusting a proximity of said opposing lateral edges.

10. The device of claim 7, wherein said adjustment mechanism comprises an inflatable member mounted between said material and the heart.

11. The device of claim 1, further comprising a securing member.

12. The device of claim 11, wherein said securing member comprises an inelastic band configured to extend along said septum when said device is in place.

13. The device of claim 11, wherein said securing member comprises a plurality of rings configured to extend along said septum when said device is in place.

14. A device according to claim 1 wherein said material is dimensioned to have a longitudinal dimension between said upper and lower ends sufficient for said jacket to constrain said valvular annulus.

15. A device according to claim 1 wherein said material encloses said apex.

16. A device according to claim 1 wherein said apex protrudes beyond said material.

17. A device according to claim 1 wherein said jacket is sized to at least partially cover and constrain said upper portion.

18. The device of claim 1, wherein the material comprises a knit.

19. A method for treating cardiac disease of a patient's heart, said heart having a longitudinal axis from an apex to a base, an upper portion and a lower portion divided by an A-V groove, a valvular annulus adjacent said A-V groove, and ventricular lower extremities adjacent said apex, said ventricular lower extremities comprising a right ventricle and left ventricle wherein said right and left ventricle are separated by a septum, said method comprising:
    surgically accessing said patient's heart;
    positioning a first component over a first ventricle, said first component comprising a piece of biomedical material having an upper end and a lower end;
    securing said first component proximate said septum;
    securing said upper end of said material of said first component to said heart;
    adjusting said first component to snugly conform to an external geometry of said heart and assume a maximum adjusted volume for said material to constrain circumferential expansion of said first ventricle beyond said maximum adjusted volume during diastole and permitting unimpeded contraction of said heart during systole;
    positioning a second component over a second ventricle, said second component comprising a piece of biomedical material having an upper end and a lower end;
    securing said second component proximate751 said septum;
    securing said upper end of said second component to said heart; and
    adjusting said second component to snugly conform to an external geometry of said second ventricle and assume a maximum adjusted volume for said material to constrain circumferential expansion of said heart beyond said maximum adjusted volume during diastole and permitting unimpeded contraction of said heart during systole.

20. The method of claim 19, wherein said right ventricle is not constrained.

21. The method of claim 19, wherein said left ventricle is not constrained.

22. The method of claim 19, further comprising adjusting a tension of said material covering said left ventricle by gathering excess material and suturing a seam on said material covering said left ventricle.

23. The method of claim 19, further comprising adjusting a tension of said material covering said right ventricle by gathering excess material and suturing a seam on said material covering said right ventricle.

24. The method of claim 19, wherein said tension of said material covering said left ventricle is greater than said tension of said material covering said right ventricle.

25. A device for treating cardiac disease of a heart having a longitudinal axis from an apex to a base, an upper portion and a lower portion divided by, an A-V groove, a valvular annulus adjacent said A-V groove, and ventricular lower extremities adjacent said apex, said ventricular lower extremities comprising a right ventricle and left ventricle wherein said right and left ventricle are separated by a septum, the device comprising:

flexible material having upper and lower ends dimensioned to cover at least said left ventricle or at least said right ventricle, wherein said material is adapted to be adjusted on said heart to snugly conform to an external geometry of said heart and constrain circumferential expansion of at least said left ventricle or at least said right ventricle during diastole and permit substantially unimpeded contraction of said heart during systole, wherein pressure exerted by said device on said right ventricle during diastole is different than pressure exerted by said device on said left ventricle during diastole; and a securing member that comprises a plurality of rings configured to extend along said septum when said device is in place.

26. The device of claim 25, wherein said material is adapted to be secured to said heart proximate said septum.

27. The device of claim 25, wherein said material is secured to said heart by fibrosis.

28. The device of claim 25, wherein said device covers said left and right ventricle.

29. The device of claim 28, wherein said device is constructed as a unitary jacket.

30. The device of claim 28, wherein said device comprises a first component comprising material configured to cover said left ventricle and a second component comprising maternal configured to cover said right ventricle, wherein said first and second components are implanted separately.

31. The device of claim 28, wherein said material covering said right ventricle has a greater compliance than said material covering said left ventricle.

32. The device of claim 28, wherein said material covering said left ventricle is under more tension than said material covering said right ventricle.

33. The device of claim 28, further comprising a first adjustment mechanism configured to adjust a tension of said material covering said right ventricle and a second adjustment mechanism configured to adjust a tension of said material covering said left ventricle, wherein the tension of the material covering said left ventricle is greater than the tension of the material covering said right ventricle.

34. The device of claim 25, further comprising at least one adjustment mechanism configured to adjust a tension of said material.

35. The device of claim 34, wherein said adjustment mechanism comprises material that is sufficiently flexible such that excess amounts of said material can be gathered following placement of said material over said heart to snugly conform said material to an external geometry of said heart.

36. The device of claim 34, wherein said adjustment mechanism comprises a slot comprising opposing lateral edges, wherein the tension of said material is adjusted by adjusting a proximity of said opposing lateral edges.

37. The device of claim 34, wherein said adjustment mechanism comprises an inflatable member mounted between said material and the heart.

* * * * *

UNITED STATES PATENT AND TRADEMARK OFFICE
CERTIFICATE OF CORRECTION

PATENT NO.     : 6,572,533 B1                                              Page 1 of 1
DATED          : June 3, 2003
INVENTOR(S)    : Shapland et al.

It is certified that error appears in the above-identified patent and that said Letters Patent is hereby corrected as shown below:

Column 5,
Line 9, "lungs; and" should read -- lungs; and --

Column 8,
Line 64, "(i.e., less)" should read -- (e.g., less) --
Line 65, "is feasibly" should read -- is feasible --

Column 9,
Line 10, "can.achieve" should read -- can achieve --

Column 14,
Line 57, "proximate 751 said" should read -- proximate said --

Column 15,
Line 18, "divided by, an" should read -- divided by an --

Column 16,
Line 10, "maternal" should read -- material --

Signed and Sealed this

Fourteenth Day of October, 2003

JAMES E. ROGAN
*Director of the United States Patent and Trademark Office*